United States Patent [19]

Kotz et al.

[11] Patent Number: 5,326,360
[45] Date of Patent: Jul. 5, 1994

[54] ENDOPROSTHESIS FOR THE KNEE JOINT

[75] Inventors: Rainer Kotz; Reinhard Windhager, both of Wien, Austria

[73] Assignee: Howmedica GmbH, Schonkirchen, Fed. Rep. of Germany

[21] Appl. No.: 983,015

[22] Filed: Nov. 30, 1992

[30] Foreign Application Priority Data

Dec. 20, 1991 [DE] Fed. Rep. of Germany ... 9115810[U]

[51] Int. Cl.⁵ .................................................. A61F 2/38
[52] U.S. Cl. .......................................... 623/20; 623/38; 403/104; 403/109; 403/327
[58] Field of Search ............... 403/104, 105, 106, 109, 403/327, 107; 623/20, 39, 38

[56] References Cited

U.S. PATENT DOCUMENTS

| | | | |
|---|---|---|---|
| 1,474,325 | 11/1923 | Kallmeyer | 403/105 X |
| 2,555,515 | 6/1951 | Slater | 403/104 X |
| 2,700,772 | 2/1955 | Davidson et al. | |
| 3,837,753 | 9/1974 | Weiste et al. | 405/327 X |
| 4,502,160 | 3/1985 | Moore et al. | |
| 4,892,546 | 1/1990 | Kotz et al. | 623/18 |

FOREIGN PATENT DOCUMENTS

| | | |
|---|---|---|
| 0290767 | 11/1988 | European Pat. Off. |
| 0350337 | 1/1990 | European Pat. Off. |
| 9115810 | 2/1992 | Fed. Rep. of Germany |
| 0703625 | 5/1931 | France ............ 403/109 |

Primary Examiner—Randall L. Green
Assistant Examiner—D. Willse
Attorney, Agent, or Firm—Peter C. Richardson; Lawrence C. Akers; Raymond W. Augustin

[57] ABSTRACT

An expandable endoprosthesis for a joint and adjacent bone parts has first and second joint component parts. The second component has a part at one end thereof for a portion of a joint. The second component has a telescoping stem coupled to its joint part for attachment to a long bone. The telescoping stem has an inner and an outer member axially adjustable with respect to one another by means of a threaded spindle and a threaded spindle nut attached respectively to either the inner or outer member. A pinion gear is attached to either the spindle or spindle nut for rotation therewith. An indexing system is provided to rotate the pinion a predetermined amount upon movement of the first and second joint components towards one another after implantation and thereby lengthen the second joint component stem.

6 Claims, 1 Drawing Sheet

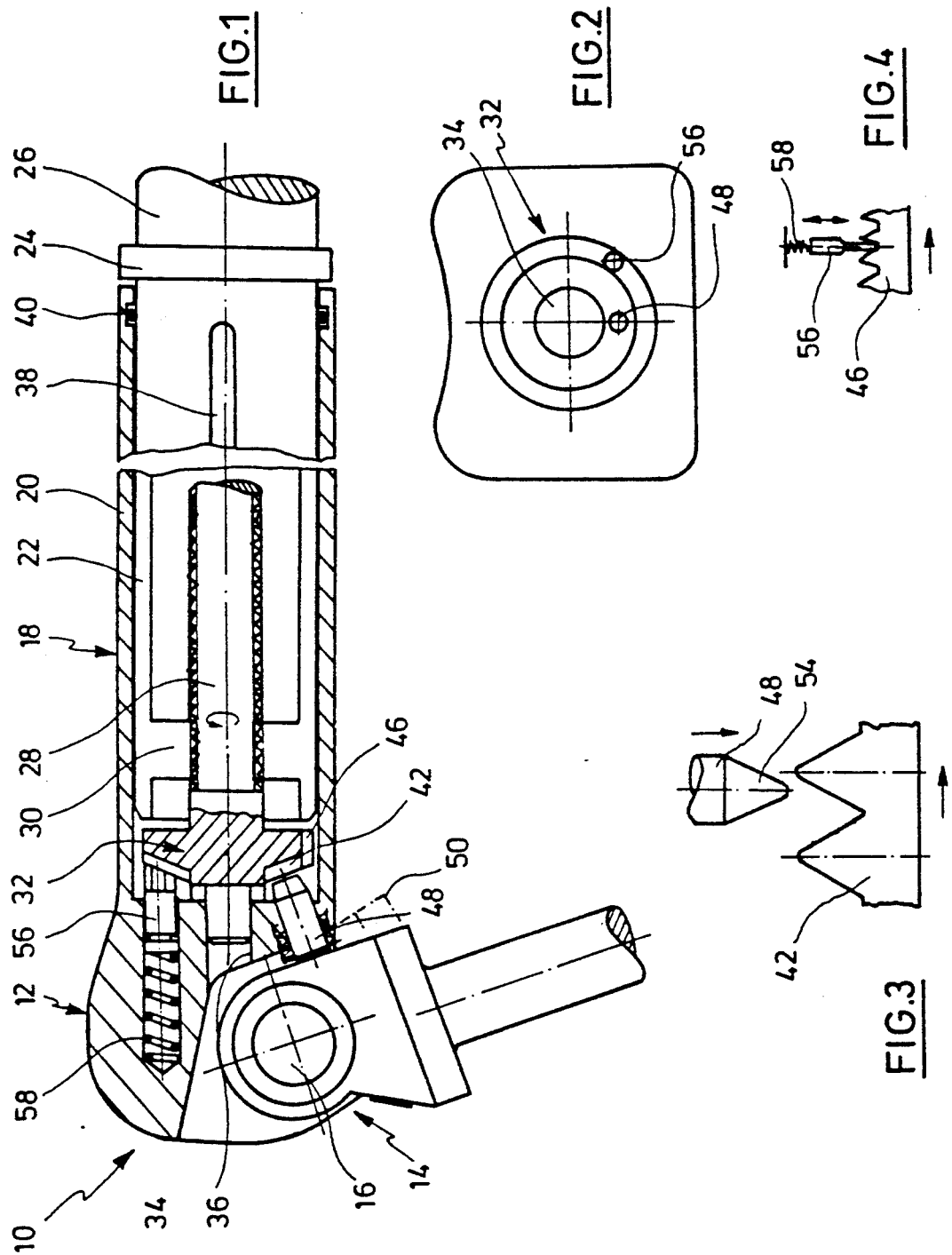

ENDOPROSTHESIS FOR THE KNEE JOINT

BACKGROUND OF THE INVENTION

1. Field of the Invention

The present invention refers to an endoprosthesis for a knee joint. More particularly, it relates to an endoprosthesis including a portion which is adjustable in length after implanting.

2. Description of the Prior Art

For patients who are still growing and who receive a total endoprosthesis for the knee joint, for example, an adaptation to the growth in length of their bones is necessary. U.S. Pat. No. 4,892,546 discloses a so-called growth prosthesis comprising a pair of telescopically co-acting rod members defining a bone replacement part, wherein a spindle and a spindle nut provide for a relative adjustment of the rod members. The spindle of the known prosthesis is coupled to a bevel gear of which a gear wheel includes a drive pin which may be actuated from outside the prosthesis. Preferably the drive pin is located in an area of the joint where the thickness of the soft tissue is relatively thin so that the bevel gear becomes accessible by a mere prick incision. Therefore, only local anesthesia is required to adjust the prosthesis in length. Nevertheless an operation, although minor, is necessary. This results in a certain stress and risk to the patient.

SUMMARY OF THE INVENTION

It is an object of the present invention to provide an adjustable-length prosthesis for the knee joint including an adjacent bone portion wherein the length may be adjusted post-operatively without an operation.

According to the invention, an index drive is provided in the prosthesis which is actuated by moving the tibial or femoral joint member to a more or less extreme bending position of the joint. An indexing member of the indexing drive directly actuates the member to be moved, i.e. a threaded spindle in steps. The indexing member is actuated in an extreme bending position which is limited by the geometry of the knee prosthesis to obtain a rotation of the threaded spindle. According to a preferred embodiment of the invention, a ratchet mechanism is provided in which typically an indexing pawl engages the teeth of an indexing wheel, whereas a locking pawl locks the indexing wheel when the driving wheel performs its return stroke.

A number of different structural embodiments can be used for the ratchet mechanism. According to one embodiment of the invention, the indexing member is a pin which is slidably supported in the femoral or tibial joint member which pin coacts with the teeth of a gear wheel. When the indexing pin is actuated by bending the joint, the gear wheel is driven at a small rotational angle. A repeated bending and stretching thus results in a corresponding stepwise turning of the threaded spindle.

When the indexing pin coacting with the tooth flanks of the gear wheel provides for an indexing of less than the circular tooth pitch, i.e. approximately one-half the tooth pitch, a spring loaded locking pawl cooperating with the teeth of the pinion is provided to rotate the pinion around half the pitch when the indexing pin is out of engagement with the teeth. Accordingly, a rotation of half the pitch is performed by the pin and the remaining rotation by the locking pawl.

According to a further embodiment of the invention, the indexing pin is biased by a spring to disengage the teeth.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 1 is a side view, partly in section, of a prosthesis according to the invention;

FIG. 2 is a front view of an indexing pinion of the prosthesis of FIG. 1;

FIG. 3 is a side view portion of the pinion of FIG. 1 in the direction of arrow 3; and FIG. 4 is a view illustrating a locking pawl coacting with the pinion of the prosthesis of FIG. 1.

DESCRIPTION OF THE PREFERRED EMBODIMENT

The endoprosthesis shown in FIG. 1 comprises a prosthetic knee joint 10 of a hinge joint type including a femoral joint portion 12 and a tibial joint portion 14. The joint portions 12, 14 are pivotally arranged about the rotating pin 16. Tibial joint portion 14 comprises any well known means (not shown) for attaching to the human tibia. A bone replacement part 18 is attached to the femoral joint portion 12. The replacement part comprises a tube 20 integrally connected to femoral portion 12 in which tube 20 has an inner cylindrical part 22 which is telescopically slidingly received. A displacement of inner part 22 into the outer part is limited by a radial flange 24. The side of flange 24 opposite part 20 is connected to a solid shaft 26 comprising means (not shown) for attaching to the femur. A suitable attachment is shown in U.S. Pat. No. 4,892,546, for example.

Inner telescopic part 22 is formed partly hollow and accommodates a threaded spindle 28 cooperating with a spindle nut which is formed by a cross-wall of the inner telescopic part 22. Spindle 28 integrally carries an indexing pinion 32 having a front end comprising a pin 34 which is rotatably supported in a bore 36 of femoral part 12.

When spindle 28 is rotated, telescopic part 22 moves relatively with respect to the telescopic part 20 to obtain a change in length. Telescopic part 22 is non-rotatably fixed by, for example, a slot and key as indicated at 38. Both the telescopic parts are sealed with respect to each other as indicated by the seal 40.

The indexing pin comprises a first bevelled tooth 42 and a second tooth 46 (see FIG. 4). The femoral part 12 slidingly supports an indexing pin 48 which can be biased by a spring (not shown) away from the indexing pinion 32. The indexing pin 48 projects beyond the femoral part 12, wherein the outwardly directed motion of pin 48 may be limited by a stop means not shown. Then tibial part 14 is further bent with respect to femoral part 12, as indicated in dash lines 50, and tibial part 14 urges indexing pin 48 towards pinion 32. Accordingly, the conical tip 54 of pin 48 engages an adjacent flank of a tooth 42 to rotate pinion 32 about half a pitch of one of the teeth 42.

A locking pawl 56, in the shape of a pin and urged by pressure spring 58 towards pinion 32, cooperates with teeth 46. When the pinion 32 is rotated as mentioned before, pawl 56 disengages the teeth. As the indexing pin 48 rotates the pinion such that teeth 46 are rotated about half the pitch or somewhat more. Locking pawl 56 can enter the next tooth gap to further rotate the pinion a predetermined amount. Repeating the steps referred to, the spindle is rotated, further resulting in the desired change of length by moving inner telescopic part 22 out of the outer part.

The artisan realizes that the indexing mechanism performs a length adaptation of the prosthesis, eliminating the need of a surgical operation.

FIG. 4 shows that the profile of the flanks of the teeth 46 are different. When the locking pawl 56 moves out against the force of the spring 58, pawl 56 slides along a profile which slopes away from the gear bottom at a predetermined angle, whereas the profile on the opposite side of the tooth in the form of a steeper almost straight inclined ramp.

While several examples of the present invention have been described, it is obvious that many changes and modifications may be made thereunto, without departing from the spirit and scope of the invention.

We claim:

1. An endoprosthesis for the knee joint and adjacent bone parts comprising a femoral and a tibial component, a bone replacement element attached to one of said femoral or tibial components which replacement element has a pair of telescopically cooperating rod members which are axially adjustable with respect to each other by a threaded spindle and a spindle nut, said spindle has a pinion mounted thereon to be rotatably actuated by an indexing mechanism comprising an indexing member mounted on said one joint component adjacent the knee joint which is moved into and out of engagement with said pinion by the movement of the tibial or femoral components to an extreme bending position of the knee joint wherein said indexing mechanism is a ratchet mechanism having a pin which is slidably supported in said one joint component for sliding engagement and disengagement therewith, which pin cooperates with teeth on said pinion, said indexing member advancing said pinion a predetermined distance; and a spring-loaded locking pawl is provided coacting with the teeth on said pinion which pawl rotates the pinion a further predetermined distance when the indexing pin disengages the teeth.

2. The endoprosthesis of claim 1 wherein the indexing pin is biased by a spring away from said teeth.

3. The endoprosthesis of claim 1 wherein each of said teeth have a tooth profile along which the locking pawl moves, which slopes away from the base of the tooth at a predetermined angle which causes the locking pawl to rotate the pinion as the pawl moves.

4. An expandable bone prosthesis comprising:
a first component having a joint part thereon;
a second component having a joint part at one end thereof, said second component having a telescoping stem extending from said joint part thereof for attachment to a bone, said telescoping stem having an inner member and an outer member axially adjustable with respect to one another by means of a threaded spindle fixedly attached to one of said inner and outer members and a threaded spindle nut fixedly attached to the other of said inner and outer members;
a pinion means attached to one of said threaded spindle or spindle nut for rotation therewith;
an indexing means for rotating said pinion means a predetermined amount upon movement of said joint components towards one another after implantation, said indexing means includes a pin which is spring mounted on said second component, said pin having a first end engageable with a surface of said first component and a second end for engaging teeth on said pinion upon engagement of said first end with said first component surface upon said movement of said joint components towards one another; and
a spring-loaded locking pawl is provided coacting with the teeth on said pinion which pawl rotates the pinion a further predetermined distance when the indexing pin disengages the teeth.

5. The endoprosthesis of claim 4 wherein the indexing pin is biased by a spring away from said teeth.

6. The endoprosthesis of claim 5 wherein each of said teeth have a tooth profile along which the locking pawl moves, which slopes away from the base of the tooth at a predetermined angle which causes the locking pawl to rotate the pinion as the pawl moves.

* * * * *